United States Patent [19]

Steiner et al.

[11] Patent Number: 5,199,870
[45] Date of Patent: Apr. 6, 1993

[54] PROCESS FOR DESTROYING AND REMOVING MATERIAL FROM TEETH

[75] Inventors: Rudolf Steiner, Ulm; Ulrich Keller, Dellmensingen; Raimund Hibst, Erbach, all of Fed. Rep. of Germany

[73] Assignee: Aesculap AG, Tuttlingen, Fed. Rep. of Germany

[21] Appl. No.: 768,655

[22] PCT Filed: Apr. 7, 1990

[86] PCT No.: PCT/EP90/00554
§ 371 Date: Oct. 10, 1991
§ 102(e) Date: Oct. 10, 1991

[87] PCT Pub. No.: WO90/11728
PCT Pub. Date: Oct. 18, 1990

[30] Foreign Application Priority Data
Apr. 11, 1989 [DE] Fed. Rep. of Germany ....... 3911871

[51] Int. Cl.$^5$ .............................................. A61C 3/00
[52] U.S. Cl. ...................................... 433/29; 433/215
[58] Field of Search .......................... 433/29, 215, 216; 606/3, 10, 13, 15, 16

[56] References Cited

U.S. PATENT DOCUMENTS 4,826,431  5/1989  Fujimura et al. ...................... 433/29
5,020,995  6/1991  Levy ..................................... 433/215

FOREIGN PATENT DOCUMENTS 0073617  3/1983  European Pat. Off. ............ 433/215
3415293  2/1987  Fed. Rep. of Germany ........ 433/29

*Primary Examiner*—John J. Wilson
*Attorney, Agent, or Firm*—Barry R. Lipsitz

[57] ABSTRACT

In a process for destroying and removing tooth material by means of pulsed infrared laser beams, in order to reduce the damage to the surrounding tissue without simultaneously impairing the effectiveness of the removal, it is propsed that prior to the irradiation with the laser beams, the tooth material be covered with a layer of liquid of between 10 and 200 micrometers thickness which absorbs the laser radiation.

14 Claims, 1 Drawing Sheet

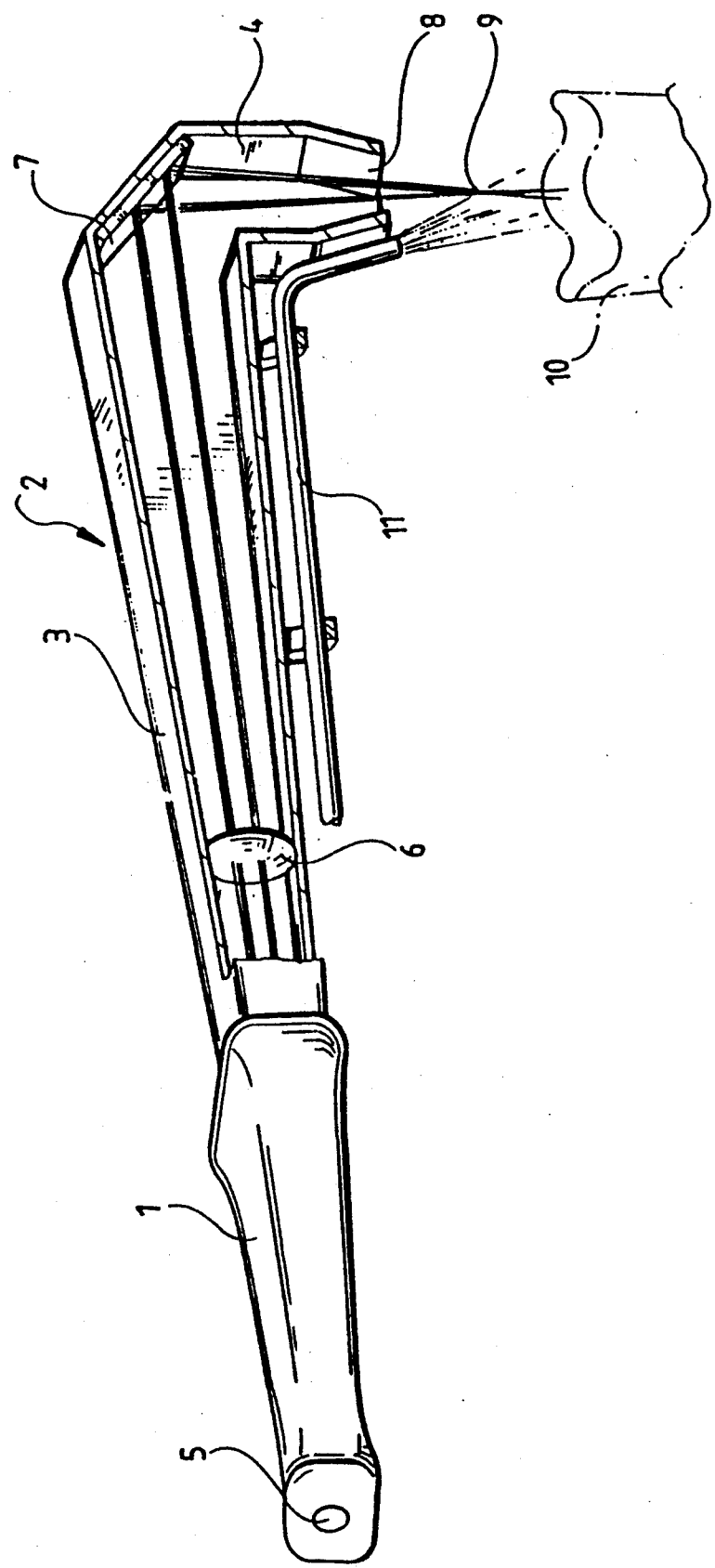

PROCESS FOR DESTROYING AND REMOVING MATERIAL FROM TEETH

BACKGROUND OF THE INVENTION

The invention relates to a process for destroying and removing tooth material by means of pulsed infrared laser beams.

It is well known that pulsed Er:YAG laser beams can be used similarly to mechanical drills to remove tooth tissue but this makes craters with very slight damage to the surrounding area in both the enamel and the dentine. The removal of dentine is more effective than the removal of enamel, and carious tissue can be particularly effectively removed (R. Hibst et al in "Laser in Medicine and Surgery"-MZV-Verlag (publisher) 4:163 to 165 (1988)).

However, light and electron microscopic examinations have shown that with use of the aforementioned pulsed infrared laser radiation, cracks and vitrification of the material surrounding the crater are avoided, but there is nevertheless a slight brownish discoloration of the crater rim in the dentine.

The object of the invention is to so improve a generic process that the remaining tissue is treated even more gently without impairing the effectiveness of the material removal by the laser radiation.

SUMMARY OF THE INVENTION

This object is accomplished in accordance with the invention in a process of the kind described at the beginning by the tooth material being covered prior to or during the irradiation with the laser beams with a layer of liquid of between 10 and 200 micrometers, in particular between 30 and 60 micrometers, thickness which absorbs the laser radiation.

Surprisingly, it has been found that with this thin layer which actually absorbs the laser radiation, there is not only no impairment of the effect of the laser radiation which produces the craters, but, at the same time, the surrounding tissue remains practically completely undamaged. There is no occurrence of a brownish discoloration of the dentine in the vicinity of the crater rim, and yet the material can be removed in the immediate area of irradiation with the same effectiveness as without the use of the liquid. The mechanism underlying the effect is not yet fully explicable, but the expansion of the vapor of the absorbing liquid occuring during the irradiation possibly leads to a particularly effective, local cooling of the tissue surrounding the drilling location.

Water is preferably used as liquid. The liquid may contain sodium chloride and/or detergents or other additives.

It is particularly advantageous for the amount of liquid applied to the tooth material per time unit to be increased as the radiation energy per laser pulse is increased. In other words, the amount of liquid applied to the tooth material and the radiation energy applied per time unit are increased and reduced in the same way in order to thereby ensure that the increased evaporation rate of the liquid upon impingement of a greater amount of radiation energy is compensated. In this way it is possible to keep the layer thickness substantially constant prior to impingement of a laser pulse, and independently of how much liquid evaporated during the previous laser pulse.

It is particularly advantageous for the liquid to be applied intermittently before each laser pulse. This ensures that prior to the laser pulses, generated approximately at a repetition rate of 1 Hz, an unheated, new layer of liquid is applied again.

It is, however, of course, also possible for the liquid to be applied continuously.

In the case of continuous application, it is, furthermore, expedient for the amount of liquid applied to the tooth material per time unit to be increased as the repetition rate of the laser pulses is increased, and vice versa. An increase in the repetition rate of the laser pulses increases the radiation energy impinging on the tooth material per time unit and hence also the liquid evaporated per time unit. To ensure constant coverage of the tooth material with the liquid, it is, therefore, advantageous to apply an increased amount of liquid to the tooth material in a corresponding manner.

BRIEF DESCRIPTION OF THE DRAWING

The FIGURE illustrates a handpiece useful in practicing the process of the present invention.

DETAILED DESCRIPTION OF THE INVENTION

Particularly uniform distribution of the liquid film with an even layer thickness is obtained by applying the liquid in the form of a spray to the tooth material.

The following description of a preferred embodiment of a handpiece suitable for the laser treatment serves in conjunction with the drawing to explain the invention in greater detail.

The handpiece illustrated in the drawing comprises a handle 1 and an L-shaped housing 2 with two legs 3 and 4, respectively, extending perpendicular to one another. The one leg 3 immediately adjoins the handle 1, the other leg 4 protrudes perpendicularly downwards at the end of the leg 3 remote from the handle 1.

A light guide, not illustrated in the drawing, for example, a glass fiber guide, is located inside the handle 1 and is connectable via a connection means 5 to a light guide likewise not illustrated in the drawing. The handle is supplied via these light guides with the pulsed infrared radiation of an Er:YAG laser with a wavelength of 2.94 micrometers, for example, with a pulse duration of 200 microseconds, radiation energies of 10 to 1000 mJ per pulse and a repetition rate of ½ to 5 Hz. This treatment radiation is concentrated in a convex lens 6 arranged at the handle end of the housing 2 and guided via a deflection mirror 7 inclined at 45° and arranged in the region of transition between the two legs 3 and 4 through an outlet opening 8 arranged at the free end of the leg 4 out of the housing 2. At a slight spacing from the outlet opening, for example, at a spacing of between 5 and 20 mm, the treatment radiation is focused so that the treatment beam 9 can impinge in the focused area on the material of a tooth 10 to be treated.

A supply line 11 is located on the underside of the housing 2 for a liquid directed at the area of the tooth 10 to be treated and sprays liquid in the form of a spray onto the tooth such that the area on which the treatment beam impinges is covered with a thin, coherent film of liquid.

This liquid can be water or another liquid which absorbs in the wavelength range of the treatment radiation, i.e., which absorbs the treatment beam. The effect may also be improved by additives to the liquid, for example, by adding detergents such as sodium lauryl sulfate which ensures even spreading of the liquid film.

The liquid is applied in the form of a spray either continuously or preferably intermittently in the cycle of the pulsation of the treatment beam so that in each case a pulse of liquid reaches the surface of the tooth to be treated before a pulse of treatment radiation.

The layer thickness of the film of water applied before each pulse of radiation should lie between 10 and 200 micrometers, preferably in the range of between 30 and 60 micrometers.

It was found that this film of liquid absorbs the treatment radiation but that the proportion that is absorbed is so low that there is practically no reduction in the removal of material in the desired area. On the other hand, the material in the surrounding area is subjected to less warming-up and less stress and so it remains substantially undamaged even directly at the rim of the resulting crater. Therefore, compared with tooth material which is not coated with an absorbing liquid, the quality of the removal is substantially higher at the same removal rate.

The repetition rate of the laser pulses is alterable. If the liquid is applied in pulses in the cycle of the laser pulse repetition rate, it is ensured that also at an altered repetition rate, the tooth material is always covered with a layer of liquid of approximately the same thickness before a laser pulse impinges on the tooth material.

If, on the other hand, the liquid is applied continuously, it is expedient to also change the amount of liquid applied per time unit in accordance with a change in the laser pulse repetition rate in order to always maintain a continuous layer thickness in accordance with the changed energy density of the impinging radiation with respect to time and hence the different evaporation rate of the liquid per time unit.

It is, furthermore, possible to change the energy content of a laser pulse, for example, by changing the laser pulse duration. In this case, too, it is expedient for the rate at which the liquid is applied to be adapted to the change in the energy of a laser pulse so that the correspondingly changed evaporation rate is just compensated. In this way coverage of the tooth material with liquid of an approximately constant layer thickness is achieved.

We claim:

1. A process for destroying and removing tooth material by means of pulsed infrared laser beams, comprising the step of covering the tooth material, prior to or during the irradiation with the laser beams, with a layer of liquid of between 10 and 200 micrometers thickness which absorbs the laser radiation.

2. A process as defined in claim 1, wherein water is used as said liquid.

3. A process as defined in claim 2, wherein said liquid contains detergents.

4. A process as defined in claim 2, wherein the amount of liquid applied to the tooth material per unit time is increased as the radiation energy per laser pulse is increased.

5. A process as defined in claim 2, wherein the liquid is applied intermittently before each laser pulse.

6. A process as defined in claim 2, wherein the liquid is applied continuously.

7. A process as defined in claim 6, wherein the amount of liquid applied to the tooth material per unit time is increased as a repetition rate of the laser pulses is increased.

8. A process as defined in claim 2, wherein the liquid is applied to the tooth material in the form of a spray.

9. A process as defined in claim 1, wherein said liquid contains detergents.

10. A process as defined in claim 1, wherein the amount of liquid applied to the tooth material per unit time is increased as the radiation energy per laser pulse is increased.

11. A process as defined in claim 1, wherein the liquid is applied intermittently before each laser pulse.

12. A process as defined in claim 1, wherein the liquid is applied continuously.

13. A process as defined in claim 12, wherein the amount of liquid applied to the tooth material per unit time is increased as a repetition rate of the laser pulses is increased.

14. A process as defined in claim 1, wherein the liquid is applied to the tooth material in the form of a spray.

* * * * *